United States Patent
Tomita et al.

(10) Patent No.: US 7,067,634 B2
(45) Date of Patent: Jun. 27, 2006

(54) METHOD FOR DIAGNOSING OR MONITORING CARBOHYDRATE METABOLISM DISORDERS

(75) Inventors: Motowo Tomita, Kanagawa (JP); Yasuko Nakano, Tokyo (JP); Hiroshi HIrose, Tokyo (JP); Koichi Matsubara, Shizuoka (JP)

(73) Assignee: Rebio Gen, Inc., Tokyo (JP)

( * ) Notice: Subject to any disclaimer, the term of this patent is extended or adjusted under 35 U.S.C. 154(b) by 0 days.

(21) Appl. No.: 10/487,039

(22) PCT Filed: Aug. 16, 2002

(86) PCT No.: PCT/JP02/08331

§ 371 (c)(1),
(2), (4) Date: Aug. 16, 2004

(87) PCT Pub. No.: WO03/016906

PCT Pub. Date: Feb. 27, 2003

(65) Prior Publication Data

US 2005/0048565 A1 Mar. 3, 2005

(30) Foreign Application Priority Data

Aug. 17, 2001 (JP) .............................. 2001-248047

(51) Int. Cl.
*C07K 16/00* (2006.01)
*G01N 33/53* (2006.01)

(52) U.S. Cl. ..................................... 530/387.1; 435/7.1
(58) Field of Classification Search ..................... None
See application file for complete search history.

(56) References Cited

U.S. PATENT DOCUMENTS 6,461,821 B1   10/2002   Matsuzawa et al.

2003/0166551 A1   9/2003   Matsuzawa et al.

FOREIGN PATENT DOCUMENTS

| EP | 1 033 134 | 9/2000 |
|---|---|---|
| WO | 01/32868 | 5/2001 |

OTHER PUBLICATIONS

Kikuko Hotta et al., *Arterioscler. Thromb. Vasc. Biol.*, No. 20, p. 1595-1599 (2000).
Arita et al., "Paradoxical Decrease of an Adipose-Specific Protein, Adiponectin, in Obesity", *Biochem. Biophys. Res. Commun.*, vol. 257, No. 1, 1999, pp. 79-83.
Nakano et al., "Isolation and Characterization of GBP28, a Novel Gelatin-Binding Protein Purified from Human Plasma", *J. Biochem.*, vol. 120, No. 4, 1996, pp. 803-812.
Weyer et al., "Hypoadiponectinemia in Obesity and Type 2 Diabetes: Close Association with Insulin Resistance and Hyperinsulinemia", *The Journal of Clinical Endocrinology & Metabolism*, vol. 86, No. 5, pp. 1930-1935, 2001.
Hotta et al., "Circulating Concentrations of the Adipocyte Protein Adiponectin Are Decreased in Parallel With Reduced Insulin Sensitvity During the Progression to Type 2 Diabetes in Rhesus Monkeys", *Diabetes*, vol. 50, pp. 1126-1133, 2001.
Yang et al., "Weight Reduction Increases Plasma Levels of an Adipose-Derived Anti-Infammatory Protein, Adiponectin", *The Journal of Clinical Endocrinology & Metabolism*, vol. 86, No. 8, pp. 3815-3819, 2001.

*Primary Examiner*—Eileen O'Hara
*Assistant Examiner*—Gyan Chandra
(74) *Attorney, Agent, or Firm*—Wenderoth, Lind & Ponack, L.L.P.

(57) ABSTRACT

This invention provides a method for diagnosing geriatric diseases associated with insulin resistance, such as type II diabetes, at an early stage and a method for monitoring the therapeutic effects of agents for type II diabetes by quantitatively assaying GBP28 with the use of a monoclonal antibody that can assay adiponectin (GBP28) in a sample.

6 Claims, 4 Drawing Sheets

SEQUENCE LISTING

<160> NUMBER OF SEQ ID NOS: 2

<210> SEQ ID NO 1
<211> LENGTH: 244
<212> TYPE: PRT
<213> ORGANISM: Homo sapiens

<400> SEQUENCE: 1

Met Leu Leu Leu Gly Ala Val Leu Leu Leu Ala Leu Pro Gly His
 1               5                  10                  15

Asp Gln Glu Thr Thr Thr Gln Gly Pro Gly Val Leu Leu Pro Leu Pro
                20                  25                  30

Lys Gly Ala Cys Thr Gly Trp Met Ala Gly Ile Pro Gly His Pro Gly
            35                  40                  45

```
His Asn Gly Ala Pro Gly Arg Asp Gly Arg Asp Gly Thr Pro Gly Glu
     50                  55                  60

Lys Gly Glu Lys Gly Asp Pro Gly Leu Ile Gly Pro Lys Gly Asp Ile
 65                  70                  75                  80

Gly Glu Thr Gly Val Pro Gly Ala Glu Gly Pro Arg Gly Phe Pro Gly
                 85                  90                  95

Ile Gln Gly Arg Lys Gly Glu Pro Gly Glu Gly Ala Tyr Val Tyr Arg
                100                 105                 110

Ser Ala Phe Ser Val Gly Leu Glu Thr Tyr Val Thr Ile Pro Asn Met
            115                 120                 125

Pro Ile Arg Phe Thr Lys Ile Phe Tyr Asn Gln Gln Asn His Tyr Asp
        130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 2
<211> LENGTH: 1804
<212> TYPE: DNA
<213> ORGANISM: Homo sapiens
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (445)..(445)
```

```
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t
<220> FEATURE:
<221> NAME/KEY: misc_feature
<222> LOCATION: (821)..(821)
<223> OTHER INFORMATION: n is a, c, g, or t
<220> FEATURE:
<221> NAME/KEY: misc_feature
<222> LOCATION: (999)..(999)
<223> OTHER INFORMATION: n is a, c, g, or t
<220> FEATURE:
<221> NAME/KEY: misc_feature
<222> LOCATION: (1099)..(1099)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1108)..(1108)
<223> OTHER INFORMATION: n is a, c, g, or t
<220> FEATURE:
<221> NAME/KEY: misc_feature
<222> LOCATION: (1111)..(1111)
<223> OTHER INFORMATION: n is a, c, g, or t
<220> FEATURE:
<221> NAME/KEY: misc_feature
<222> LOCATION: (1675)..(1675)
<223> OTHER INFORMATION: n is a, c, g, or t
<220> FEATURE:
<221> NAME/KEY: misc_feature
<222> LOCATION: (1800)..(1800)
<223> OTHER INFORMATION: n is a, c, g, or t

<400> SEQUENCE: 2
```

| | | | | | |
|---|---|---|---|---|---|
| ataaaatata | acgggagggg | nccataaatg | cccaccaaaa | aggccaggat | tttntggtgt | 60 |
| ttttctcttt | ttcctaacaa | agtgtttctc | cccccctnttc | tctttttttt | ttggttttgt | 120 |
| tgtttcatgt | gtcaatttaa | ttacccatat | caaantgtcc | ccaggagagg | gtagagaaga | 180 |
| aagagaatga | gagataagaa | ggaggataga | cacagaaaat | gagagagaag | ggggaaagaa | 240 |
| aaagaggaaa | ggagccagag | gagagaagct | ggttagcatt | gaatggagca | atctgtgtca | 300 |
| tcgtacttgg | gaaacccaag | gatggattct | tgncaagtcg | actcttggag | ctttccctgt | 360 |
| gcttggtcct | gtgctcagac | atgggaaaat | tagaggagtg | tcatctgtgc | aatcactgaa | 420 |
| ttcataatct | tgntnaggaa | anganactac | acacagggaa | taatgctaag | tattacagat | 480 |
| ttcagggcag | aaagagatca | aggtgggctg | caatattcag | aaaagtcttc | ctggaaaagt | 540 |
| tgaatactta | gaaagcagct | cctagaagta | gactctgctg | agatggacgg | agtccttgt | 600 |
| aggtcccaac | tgggtgtgtg | tgtggggtct | gtctctccat | ggctgacagt | gcacatgtgg | 660 |
| attccaataa | aatataacgg | gagggncca | taaatgccca | ccaaaaggc | caggattttn | 720 |
| tggtgttttt | ctcttttttcc | taacaaagtg | tttctccccc | ctnttctctt | ttttttttgg | 780 |
| ttttgttgtt | tcatgtgtca | atttaattac | ccatatcaaa | ntgtcccag | gagagggtag | 840 |
| agaagaaaga | gaatgagaga | taagaaggag | gatagacaca | gaaaatgaga | gagaagggg | 900 |
| aaagaaaaag | aggaaaggag | ccagaggaga | gaagctggtt | agcattgaat | ggagcaatct | 960 |

```
                                        -continued gtgtcatcgt  acttgggaaa  cccaaggatg  gattcttgnc  aagtcgactc  ttggagcttt    1020
ccctgtgctt  ggtcctgtgc  tcagacatgg  gaaaattaga  ggagtgtcat  ctgtgcaatc    1080
actgaattca  taatcttgnt  naggaaanga  nactacacac  agggaataat  gctaagtatt    1140
acagatttca  gggcagaaag  agatcaaggt  gggctgcaat  attcagaaaa  gtcttcctgg    1200
aaaagttgaa  tacttagaaa  gcagctccta  gaagtagact  ctgctgagat  ggacggagtc    1260
ctttgtaggt  cccaactggg  tgtgtgtgtg  gggtctgtct  ctccatggct  gacagtgcac    1320
atgtggattc  caggctcagg  atgctgttgc  tgggagctgt  tctactgcta  ttagctctgc    1380
ccggtcatga  ccaggaaacc  acgactcaag  ggcccggagt  cctgcttccc  ctgcccaagg    1440
gggcctgcac  aggttggatg  gcgggcatcc  cagggcatcc  gggccataat  ggggccccag    1500
gccgtgatgg  cagagatggc  accoctggtg  agaagggtga  gaaaggagat  ccaggtaaga    1560
atgtttctgg  cctctttcat  cacagacctc  ctacactgat  ataaactata  tgaagtcatt    1620
cattattaac  taaggcctag  acacagggag  aaagcaaagc  ttggcgtaat  catgntcatg    1680
taagaatgtt  tctggcctct  ttcatcacag  acctcctaca  ctgatataaa  ctatatgaag    1740
tcattcatta  ttaactaagg  cctagacaca  gggagaaagc  aaagcttggc  gtaatcatgn    1800
tcat                                                                     1804
```

METHOD FOR DIAGNOSING OR MONITORING CARBOHYDRATE METABOLISM DISORDERS

TECHNICAL FIELD

The present invention relates to a method for diagnosing or monitoring carbohydrate metabolism disorders by assaying adiponectin (GBP28) in a sample, a method for monitoring the therapeutic effects of agents for type II diabetes by assaying GBP28 in a sample, a method for assaying GBP28 characterized by assaying naturally-occurring GBP28 in a sample, and a monoclonal antibody that specifically reacts with naturally-occurring GBP28.

BACKGROUND ART

The number of patients afflicted with diabetes is as many as 100,000,000 or more throughout the world, and 90% or more thereof are afflicted with type II diabetes (Schoonjans, K. and Auwerx, J., Lancet 355: 1008–1010, 2000). Type II diabetes is characterized by impaired insulin secretion and/or insulin resistance (DeFronzo, R, A. ct al., Diabetes Care 15: 318–368, 1992). Thiazolidinediones had been found both in animal experiments and in clinical studies to improve insulin resistance. When such agents were administered to patients with type II diabetes, insulin action was elevated. This adversely resulted in lowered levels of blood glucose, glycohemoglobin, and serum insulin (Schwartz, S. et al., N. Engl. J. Med. 338: 861–866, 1998).

Adiponectin, which is a plasma protein derived from the adipocyte (Maeda, K. et al., Biochem. Biophys. Res. Commun. 221: 286–289, 1996; Arita, Yet al., Biochem. Biophys. Res. Commun. 257: 79–83, 1999) (also known as a gelatin-binding protein of 28 kDa (GBP28) (Nakano, Y. et al., J. Biochem. 120: 803–812, 1996; Saito, K. et al., Gene 229: 67–73, 1999; Saito, K. et al., Biol. Pharm. Bull. 22: 1158–1162, 1999)), adheres to a damaged vascular wall in vitro, blocks endodermal NF-κB signal transmission (Ouchi, N. et al., Circulation 102: 1296–1301, 2000), and inhibits cell proliferation of smooth muscles induced by HB-EGF and PDGF (Matsuzawa, Y. et al., Ann. N. Y. Acad. Sci. 892: 146–154, 1999). In the case of obesity patients, the levels of this protein in serum had been reported to be low (Arita Y. et al., Biochem. Biophys. Res. Commun. 257: 79–83, 1999). In the case of patients with type II diabetes and those of coronary artery diseases, the aforementioned serum levels had been reported to be lowered (Hotta, K. et al., Arterioscler Thromb. Vasc. Biol. 20: 1595–1599, 2000).

In the past, blood glucose, $HbA_{IC}$, serum insulin, HOMA-IR, and the like had been known as factors associated with type II diabetes. These factors were, however insufficient in terms of operability and/or sensitivity as indicators for diagnosing type II diabetes or for monitoring therapeutic effects. As mentioned above, association of GBP28 with type II diabetes had been also suggested. However, it was not sufficiently clarified whether or not GBP28 was actually applicable to the diagnosis of type II diabetes and the monitoring of therapeutic effects in the clinical field.

The ELISA technique of Ohmoto et al. is known as a method for assaying GBP28 (Ohmoto et al., BIO Clinica 15(10) 758–761, 2000; Japanese Laid-open Patent Publication (Kokai) No. 200-304748). Naturally occurring GBP28 in blood is constituted by 3 monomers, and 4 to 6 trimers are aggregated (J. Biochem. 120, 803–812, 1996). However, the process of the aforementioned conventional technique was complicated due to the use of a monoclonal antibody to GBP28 having a monomeric structure. This required naturally occurring GBP28 in a sample to be denatured, a specimen to be mixed with an SDS solution at the time of assay, and thermal treatment to be conducted at 100° C. This conventional technique was to assay the naturally occurring GBP28 in a denatured state. Therefore, it could not directly assay the GBP28 in its natural state.

SUMMARY OF THE INVENTION

In order to overcome the above problems, the present inventors have assayed the blood concentrations of a variety of parameters associated with type II diabetes in the patients with this ailment. They have also conducted concentrated studies in order to search for factors that could be clinical indicators for the diagnosis of carbohydrate metabolism disorders, such as type II diabetes, and the monitoring of therapeutic effects of agents for type II diabetes. As a result, they have found that the assay of GBP28 was very effective for the diagnosis of carbohydrate metabolism disorders and for the monitoring of the therapeutic effects of the agents therefor as described in the Examples below. They have also found that GBP28 in a sample can be simply and rapidly assayed in its natural state by assaying the GBP28 in an aggregated form. This has led to the completion of the present invention.

More specifically, the present invention provides the following (1) to (13).

(1) A method for diagnosing or monitoring carbohydrate metabolism disorders by assaying adiponectin (GBP28) in a sample.

(2) The method according to (1) above, wherein the carbohydrate metabolism disorder is type II diabetes.

(3) The method according to (1) or (2) above, wherein the GBP28 is of a naturally occurring type.

(4) A method for monitoring the therapeutic effects of agents for type II diabetes by assaying GBP28 in a sample.

(5) The method according to (4) above, wherein the GBP28 is of a naturally occurring type.

(6) The method according to (4) or (5) above, wherein the agents for type II diabetes are thiazolidine derivatives.

(7) The method according to (5) or (6) above, wherein the assay is conducted through antigen-antibody reactions.

(8) A method for assaying GBP28, wherein naturally-occurring GBP28 in a sample is assayed.

(9) The method according to any of (1) to (8) above, wherein GBP28 is assayed using a monoclonal antibody that specifically reacts with naturally occurring GBP28.

(10) The method according to (9) above, wherein the monoclonal antibody used is produced from hybridoma FERM BP-7660 or FERM BP-7661.

(11) The method according to any of (1) to (10) above, wherein GBP28 is assayed by the solid phase method, competitive assay, agglutination assay, turbidimetric assay, or sandwich enzyme immunoassay.

(12) The method according to any of (1) to (11) above, wherein the sample is serum, plasma, synovial fluid, pleural effusion, tissue extract, tissue, culture supernatant, or urine.

(13) A monoclonal antibody that specifically reacts with naturally occurring GBP28 having a trimer structure of GBP28 and/or a structure of aggregated GBP28 trimers.

(14) The monoclonal antibody according to (13) above, which is produced from hybridoma FERM BP-7660 or FERM BP-7661.

(15) A kit for assaying naturally occurring GBP28 in a sample, which comprises a monoclonal antibody that specifically reacts with naturally occurring GBP28.

This description includes part or all of the contents as disclosed in the description and/or drawings of Japanese Patent Application No. 2001-248047, which is a priority document of the present application.

BEST MODES FOR CARRYING OUT THE INVENTION

Figure 1:
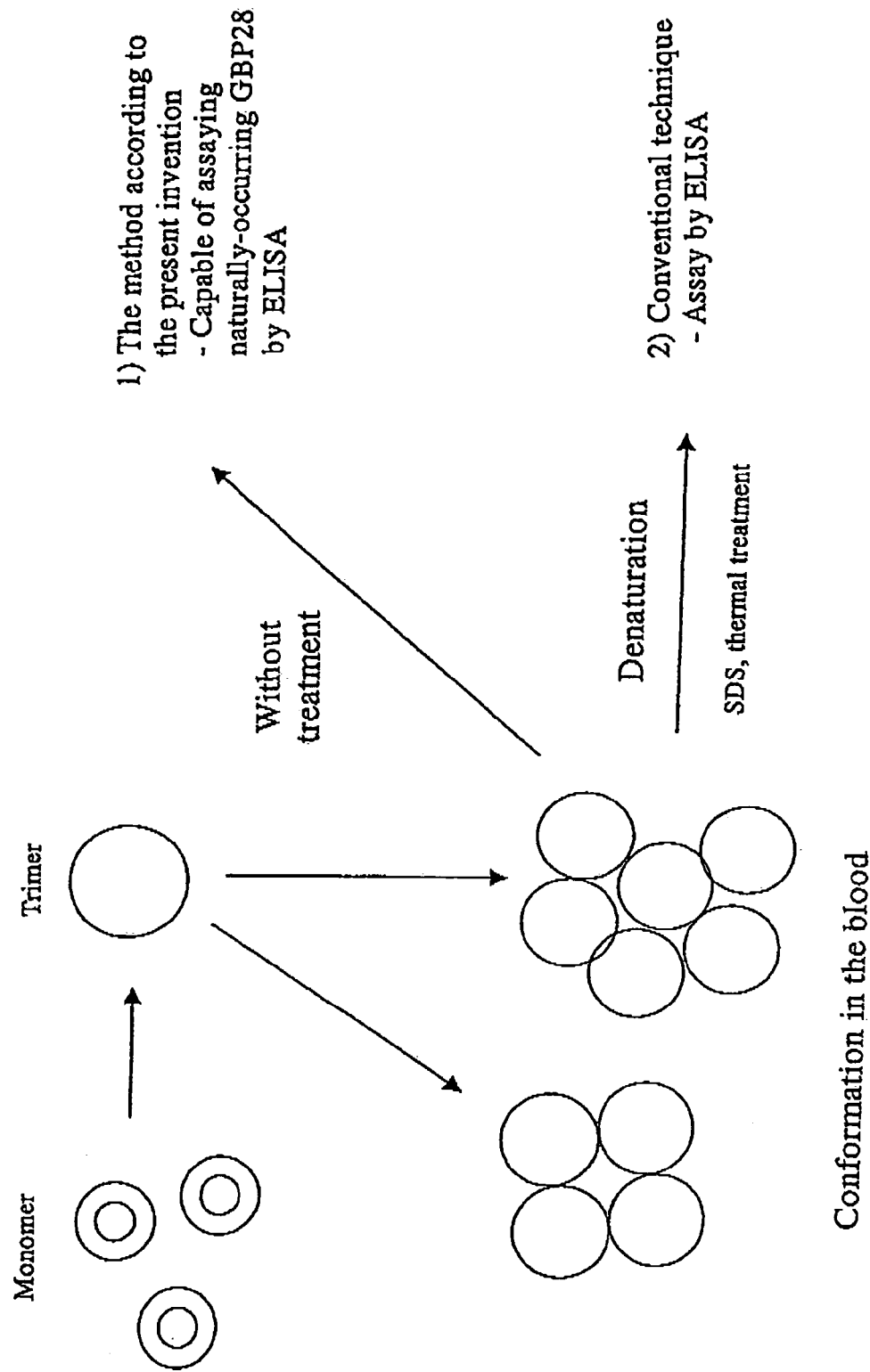
FIG. 1 schematically shows principles of the method according to the present invention and those of conventional techniques.

GBP28 in humans is known to have the amino acid sequence as shown in SEQ ID NO: 1 and the nucleotide sequence as shown in SEQ ID NO: 2. GBP28 in the blood is known to form 4 to 6 aggregated trimers, each thereof being constituted by 3 monomers (J. Biochem. 120, 803–812, 1996).

The present inventors have found that the concentration of GBP28 in a sample such as blood obtained from a healthy subject would exhibit a correlation with levels of insulin associated with an indicator of insulin resistance, insulin resistance index (HOMA-IR), triglyceride, HDL-cholesterol, and LDL-cholesterol that are characteristics of type II diabetes. They have also found that the concentration of GBP28 in a sample such as blood obtained from a patient with type II diabetes exhibited more significant changes compared with levels of plasma glucose, $HbA_{IC}$, serum insulin, and HOMA-IR that have been employed as indicators for type II diabetes when monitoring the therapeutic effects of agents for type II diabetes used-therefor. Based on these findings, the concentration of GBP28 in a sample such as blood was found to be very effective as a novel indicator for the diagnosis of carbohydrate metabolism disorders, such as type II diabetes, and the monitoring of the therapeutic effects of agents for type II diabetes.

Accordingly, the present inventors provide a method for diagnosing carbohydrate metabolism disorders such as type II diabetes and a method for monitoring the therapeutic effects of agents for type II diabetes by assaying GBP28, preferably naturally-occurring GBP28, in a sample.

In the present invention, examples of the "sample" include, but are not limited to, serum, plasma, synovial fluid, pleural effusion, tissue extract, tissue, culture supernatant, and urine.

Examples of carbohydrate metabolism disorders include diabetes (type I or II diabetes) and diabetic complications (elevated blood pressure, hyperlipidemia, arteriosclerosis, or glaucoma). The present invention is particularly suitable for the diagnosis of type II diabetes or for the monitoring of the therapeutic effects of the agents.

A variety of conventional agents can be used as therapeutic agents for carbohydrate metabolism disorders. Examples of therapeutic agents for type II diabetes include: sulfonylurea agents such as glibenclamide, gliclazide, tolbutamide, and glimepiride; immediate-release agents for accelerating insulin secretion such as nateglinide; α-glucosidase inhibitors such as voglibose and acarbose; agents for improving insulin resistance such as pioglitazone; and biguanides such as metformin. These agents can be suitably used in the method according to the present invention. Examples of particularly preferable therapeutic agents for type II diabetes include thiazolidine derivatives such as pioglitazone and troglitazone.

Methods for assaying GBP28 are not particularly limited. Assay can be conducted by any conventional method in the art such as the solid phase method, competitive assay, agglutination assay, turbidimetric assay, or sandwich enzyme immunoassay using a monoclonal antibody that specifically reacts with GBP28, preferably naturally-occurring GBP28 having a trimer structure of GBP28 and/or a structure of aggregated GBP28 trimers. Particularly preferably, assay is conducted by solid-phase enzyme-linked immunosorbent assay (ELISA). Enzyme immunoassay is a common technique in the art, and a person skilled in the art can perform it using an antibody that specifically reacts with the aforementioned GBP28.

When using a monoclonal antibody that specifically reacts with naturally occurring GBP28 in the aforementioned assay, denatured or monomeric GBP28, which does not exist in a natural state, can be excluded from the assay. More specifically, a monoclonal antibody recognizing a site that first appears in a trimer when the GBP28 forms a collagen-like conformation is particularly preferably prepared and used.

FIG. 1 schematically shows principles of the method according to the present invention for assaying GBP28 and those of conventional techniques. In the conventional technique, GBP28 that was expressed by gene recombinant *E. coli* is used as an immunogen in order to obtain a monoclonal antibody to GBP28. Since the recombinant GBP28 is present as an inclusion body in the *E. coli*, however, the protein must be processed with, for example, guanidine hydrochloride, urea, or a reducing agent when it is subjected to purification. Thus, denatured and monomeric GBP28 is the only type that can be used as an immunogen. Accordingly, the resulting monoclonal antibody reacts only with denatured and monomeric GBP28. When assaying naturally occurring GBP28 in the sample, therefore, it must be previously denatured into monomeric GBP28. In contrast, the method according to the present invention employs a monoclonal antibody that specifically reacts with naturally occurring GBP28. Thus, assay can be conducted without processing naturally occurring GBP28 in the blood.

The monoclonal antibody according to the present invention can be obtained by a technique common in the art using, for example, naturally-occurring GBP28 as an antigen. Naturally occurring GBP28 can be purified by, for example, passing a large amount of human plasma through a gelatin-cellulofine column (J. Biochem 120, 803–812, 1996), utilizing its gelatin-binding properties. For example, an animal is immunized with this naturally occurring GBP28, and a spleen or lymph node is collected from the immunized animal. Antibody-producing cells contained in the spleen or lymph node are allowed to fuse with myeloma cells with the aid of polyethylene glycol or the like to prepare hybridomas.

A hybridoma of interest is screened for, this hybridoma is cultured, and a monoclonal antibody can be prepared from the culture supernatant. Culture may be carried out in vitro or in vivo. For example, a hybridoma is administered to a mouse or the like intraperitoneally, and an antibody of interest can be then obtained from its ascites. A monoclonal antibody can be purified by, for example, fractionation with ammonium sulfate precipitation or anion chromatography or affinity purification using protein A or immobilized antigen. The thus prepared antibody is used for assaying GBP28, and it can be also applied to the antibody treatment or the like of diseases caused by abnormal expression of GBP28.

An anti-GBP28 monoclonal antibody that can be particularly preferably used in the present invention is characterized as follows:

the myeloma cell line used: P3U1;

the antigen: a solution of GBP28 (about 50 μg) isolated and purified from human serum is micellized with a complete adjuvant, the resultant is administered to a mouse intraperitoneally, two weeks later, the mouse is subjected to booster, the spleen is extirpated 3 days thereafter, and the B-cell is collected;

the number of clones where the monoclonal antibody is prepared: 3 (1H, 5, 6, and 7);

the Ig type: entirely IgGκ-type; and the epitope: it recognizes only GBP28 trimers that were not thermally denatured, and accordingly, this site is considered to first appear in the trimer when a collagen-like conformation is formed.

Hybridomas IH-6 and IH-7 producing an anti-GBP28 monoclonal antibody that can be suitably used in the present invention have been deposited at the International Patent Organism Depositary of the National Institute of Advanced Industrial Science and Technology (Tsukuba Central 6, 1-1-1 Higashi, Tsukuba, Ibaraki, Japan) as of Jul. 12, 2001, under the accession numbers FERM BP-7660 and FERM BP-7661, respectively.

Specifically, a method for diagnosing carbohydrate metabolism disorders by assaying GBP28 in the sample and a method for monitoring the therapeutic effects of the therapeutic agents can be conducted, for example, in the manner as described below.

1) Assay of the Concentration of GBP28

Serums or the like collected from patients or the like are diluted, the diluted serums or the like are added to a 96-well microtiter plate coated with a mouse anti-GBP28 monoclonal antibody, and GBP28 in the serum is allowed to bind to the mouse anti-GBP28 monoclonal antibody in the well. After the well is washed, an enzyme-labeled mouse anti-GBP28 monoclonal antibody is added and then allowed to bind to the mouse anti-GBP28 monoclonal antibody existing in the well. After the well is further washed, a substrate solution of the enzyme is added to develop color. After the termination of color development, the absorbance is assayed. In advance, the absorbance of the GBP28 standard solution at a known concentration level is assayed in the same manner, the calibration curve for the absorbance relative to the concentration of GBP28 is prepared, and the assayed absorbance is converted into the concentration of GBP28 based on the calibration curve. Thus, the concentration of GBP28 in the serums or the like collected from patients or the like can be assayed.

2) A Method for Diagnosing or Monitoring Carbohydrate Metabolism Disorders

When employing GBP28 as the indicator for diagnosing carbohydrate metabolism disorders such as type II diabetes, for example, the concentration of GBP28 that was assayed by the above method is compared with the normal value or boundary value, which had been previously calculated.

3) A Method for Monitoring the Therapeutic Effect of an Agent

When employing GBP28 as an indicator for monitoring the therapeutic effects of a therapeutic agent for type II diabetes, for example, blood is sampled from a patient with type II diabetes before and after the initiation of treatment, GBP28 is assayed by the above method, and the rate of changes in the GBP28 content of the blood from before the initiation of treatment to after the initiation of treatment is calculated, thereby evaluating the therapeutic effects. If the blood concentration of GBP28 after the initiation of the treatment is elevated compared with that before the treatment, the therapeutic effects of the agents can be recognized. The interval for blood sampling in this case is preferably between 1 and 3 months.

The present invention also provides a kit for assaying naturally occurring GBP28 in the sample comprising a monoclonal antibody that specifically reacts with naturally-occurring GBP28. The kit according to the present invention may suitably comprise, in addition to the above-mentioned antibody according to the present invention, for example, a buffer, a secondary antibody labeled with a label such as peroxidase, a standard solution, a block solution, an enzyme substrate solution such as peroxidase, and a washing liquid. The monoclonal antibody according to the present invention recognizes the trimer structure of GBP28. Accordingly, sandwich assay can be conducted by immobilizing a non-labeled monoclonal antibody on the plate, adding a GBP28-containing sample, and then using a labeled monoclonal antibody of the same type.

EXAMPLES

The present invention is hereafter described in greater detail with reference to the following examples, although the present invention is not limited to these examples.

In the following examples, all the statistical analyses were conducted using the StatView® program for Macintosh (version 4.5-J, Abacus Concepts Inc., Berkeley, Calif.). For the comparison of the baseline and the trace data for 3 months, a Wilcoxon Signed-Rank Test (two-tailed) was conducted. For the comparison of the rate of change in GBP28 and other parameters, significance was evaluated using Pearson's correlation coefficient and the partial correlation coefficient. Serum insulin, TG, and GBP28 levels and HOMA-IR would be normally distributed upon the log conversion in a large-scale study. Thus, logarithmic values were employed for the analyses regarding these parameters. All the data are represented by "mean±S.D." When p was smaller than 0.05, it was determined to be statistically significant.

Example 1

Assay of Each Parameter 10 male patients with type II diabetes (ages: 40 to 66, 57.7±7.4) either being only under diet therapy (n=7) or being under diet therapy and on medication of sulfonylurea (n=3) were subjected to inspection regarding the following parameters before and after a three-month administration of a thiazolidine derivative, pioglitazone. Body weights, blood glucose levels, and blood pressure levels of those patients and treatments for them were at constant levels for at least 3 months before the examination. The sulfonylurea doses for 3 patients were at constant levels during that period. Pioglitazone was administered to all 10 patients after breakfast every day (orally, 30 mg/day). The ages, the body mass indices (BMI), and the clinical profiles of patients at the time of initiation are shown in Table 1.

TABLE 1

Clinical Profiles of Patients with Type II Diabetes

| Parameter | | Range |
|---|---|---|
| N | 10 | |
| Age (years) | 57.4 ± 7.4 | [ 40–66 ] |
| Height (cm) | 164.2 ± 5.2 | [ 156.0–171.6 ] |
| Weight (kg) | 71.3 ± 9.8 | [ 57.3–85.1 ] |
| Body mass index (kg/m$^2$) | 26.4 ± 3.2 | [ 22.4–32.5 ] |
| Duration of disease (years) | 7.0 ± 4.5 | [ 2.0–15.0 ] |
| Glucose (mmol/l) | 8.6 ± 1.4 | [ 6.9–11.3 ] |
| HbA$_{1c}$ (%) | 6.7 ± 0.8 | [ 5.3–8.2 ] |

Data are represented by n or mean ± S.D..

In the table, data are represented by n or mean (±S.D.).

The systolic blood pressure (SBP) and the diastolic blood pressure (DBP) were measured twice in a sitting position after an at least 5-minute recess. Body heights, weights, and levels of fasting plasma glucose (FPG), HbA$_{IC}$, serum insulin, adiponectin, total cholesterol (TC), triglyceride (TG), HDL-cholesterol, LDL-cholesterol, and uric acid were measured in the morning after an overnight fast. Levels of plasma glucose, lipids, and uric acid were measured by a common automated measuring technique. The serum concentration of insulin was measured using a commercially available kit, EIA (Tosoh, Tokyo), as already described (Kawai, T. et al., Metabolism 48: 1102–1107, 1999; Hirose, H. et al., Clin. Sci. (Colch) 94: 633–636, 1998; Hirose, H. et al., J. Hypertens. 16: 2007–2012, 1998; Hirose, H. et al., Clin. Sci. (Colch) 100: 145–150, 2001). The insulin resistance index was evaluated by the Homeostasis model assessment (HOMA-IR) (Matthews, D. R. et al., Diabetologia 28: 412–419, 1985; Rudenski, A. S. et al., Metabolism 40: 908–917, 1991).

The results are shown in Table 2.

TABLE 2

Effects of three-month administration of pioglitazone on each parameter

| Parameter | Baseline | After the three-month trace | Rate of change in 3 months |
|---|---|---|---|
| N | 10 | 10 | |
| Body Mass Index (kg/m$^2$) | 26.4 ± 3.2 | 27.0 ± 3.5 | *2.1 ± 2.2 |
| Body mass index at systolic blood pressure (kg/m$^2$) | 149 ± 18 | 138 ± 15 | **-7.0 ± 4.9 |
| Body mass index at diastolic blood pressure (kg/m$^2$) | 89 ± 13 | 83 ± 9 | *-6.3 ± 6.9 |
| Fasting blood glucose (mmol/l) | 8.6 ± 1.4 | 7.0 ± 1.0 | **-18.2 ± 9.3 |
| HbA$_{1c}$ (%) | 6.7 ± 0.8 | 6.1 ± 0.6 | *-9.0 ± 8.8 |
| Serum insulin (pmmol/l) (log) | 54 ± 11 | 30 ± 8 | **-23.7 ± 13.5 |
| HOMA-IR (log) | 3.4 ± 1.9 | 1.6 ± 1.3 | *-62.6 ± 22.6 |
| Total cholesterol (mg/dl) | 208 ± 26 | 218 ± 35 | 4.8 ± 10.9 |
| Triglyceride (mg/dl) (log) | 134 ± 2 | 127 ± 2 | -1.0 ± 6.3 |
| HDL cholesterol (mg/dl) | 51.7 ± 9.4 | 52.1 ± 7.3 | 2.0 ± 11.2 |
| LDL cholesterol (mg/dl) | 124 ± 24 | 138 ± 24 | *12.3 ± 12.8 |
| Uric acid (mg/dl) | 5.9 ± 1.1 | 5.6 ± 1.3 | -5.0 ± 9.5 |
| GBP28 (μg/l) (log) | 4.8 ± 1.7 | 14.4 ± 2.1 | **80.9 ± 58 |

Data are represented by n or mean ± S.D..
*P < 0.05 (Wilcoxon test)
**P < 0.01 (Wilcoxon test)

In the table, data are represented by n or mean (±S.D.).

As shown in Table 2, a three-month administration of pioglitazone resulted in significantly lowered levels of systolic blood pressure, diastolic blood pressure, fasting plasma glucose, HbA$_{IC}$, serum insulin, and HOMA-IR. The body mass index (BMI) and the LDL-cholesterol level were elevated, although there was no significant change in levels of triglyceride, HDL-cholesterol, or uric acid.

Effects of controlling blood glucose and blood pressure levels were observed similarly with the case of troglitazone (Kawai, T. et al., Metabolism, 48: 1102–1107, 1999), unlike the case of the control group that was subjected to diet therapy. Concerning the effects of thiazolidinedione on blood pressure levels, troglitazone has been reported to lower blood pressure levels in experiments using insulin-resistant animals (Yoshioka, S. et al., J. Hypertens 18: 1857–1864, 2000) and in clinical study (Ogihara, T. et al., Am. J. Hypertens. 8: 316–320, 1995). Concerning the effects on LDL-cholesterol, administration of troglitazone (Schwartz, S. et al, N. Eng. J. Med. 338; 861–866, 1998) or rosiglitazone (Balfour, J. A. and Plosker, G. L., Drugs 57: 921–930, 1999) has been reported to be associated with the elevation of LDL-cholesterol. The LDL-cholesterol level was slightly increased by the administration of pioglitazone. It was more significant 3 months later.

Example 2

Assessment of Body Fat Distribution

The patients who had been also employed in Example 1 were subjected to the assessment of body fat distribution before and after the three-month administration of pioglitazone. Distributions of subcutaneous fat and visceral fat were determined by assessing the region of a Hounsfield unit of −150 to −50 by a method modified from the computerized tomography (CT) scan at the level of the navel by Tokunaga et al. (Tokunaga, K. et al., Int. J. Obes. 7: 437–445, 1983). CT images at the baseline and after a three-month treatment were taken in accordance with the same protocols that had been previously reported by the present inventors (Kawai, T. et al., Metabolism, 48: 1102–1107, 1999). The V/S ratio was calculated by dividing the visceral fat area (VFA) by the subcutaneous fat area (SFA). The results are shown in Table 3.

TABLE 3

Effect of three-month administration
of pioglitazone on body fat distribution

| Parameter | Baseline | After the three-month trace | Rate of changes in 3 months |
|---|---|---|---|
| N | 10 | 10 | |
| Visceral Fat Area (cm$^2$) | 165 ± 38 | 180 ± 46 | 11.3 ± 21.3 |
| Subcutaneous Fat Area (cm$^2$) | 155 ± 69 | 179 ± 81 | *16.1 ± 18.7 |
| V/S ratio | 1.2 ± 0.3 | 1.1 ± 0.3 | −4.0 ± 11.2 |

Data are represented by n or mean ± S.D..
*P < 0.05 (Wilcoxon test)

In the table, data are represented by n or mean (±S.D.).

As shown in Table 3, BMI and the subcutaneous fat area (SFA) significantly increased after the three-month administration of pioglitazone. This result was substantially the same as that obtained by the administration of troglitazone (Kawai, T. et al., Metabolism, 48: 1102–1107, 1999; Kelly, I. E. et al., Diabetes Care 22; 288–293, 1999; Mori, Y. et al., Diabetes Care 22: 908–912, 1999). On the contrary, the visceral fat area (VFA) was not reduced, but it rather slightly increased. This was different from the findings obtained based on the administration of troglitazone. Although the reason for such difference has not been elucidated yet, it could be due to structural differences such as the vitamin E structure of troglitazone and/or functions of PPARα. VFA tended to be larger while the V/S ratio tended to be smaller. However, there was no statistical significance in these differences.

Example 3

Assay of GBP28

The patients who had been employed in Example 1 were also subjected to an assay of the blood concentration of GBP28 before and after the three-month administration of pioglitazone.

The anti-human GBP28 monoclonal antibody was prepared in the following manner. First, a solution of GBP28 (about 50 μg) isolated and purified from human serum was micellized with a complete adjuvant, and the resultant was administered to a mouse intraperitoneally. Two weeks later, the mouse was subjected to booster, the spleen was extirpated 3 days thereafter, and the B-cell was collected. The B-cell and the myeloma cell were allowed to fuse with each other to prepare hybridomas, and a hybridoma of interest was administered to a mouse intraperitoneally. Thereafter (20 days later), ascites was processed with DEAE-Sepharose Fast Flow, and the monoclonal antibody of interest was obtained.

GBP28 was assayed by ELISA in the following manner. A standard GBP28 sample, a 441-fold-diluted unknown sample, and a control sample (100 μl each) were added to a 96-well microtiter plate coated with the mouse anti-GBP28 monoclonal antibody. The plate was incubated for 60 minutes, the well was washed, and incubation was carried out for additional 30 minutes with the horseradish peroxidase-labeled mouse anti-GBP28 monoclonal antibody. The plate was washed again, and incubation was carried out for 30 minutes with a tetramethylbenzidine reagent. Subsequently, 100 μl of aqueous solution of 0.36N sulfuric acid was added to each well to terminate the reaction, and the absorbance at 450 nm was assayed. Intra- and interassay coefficients were 4.8% to 4.9% and 3.3% to 6.8%, respectively.

Figure 2:
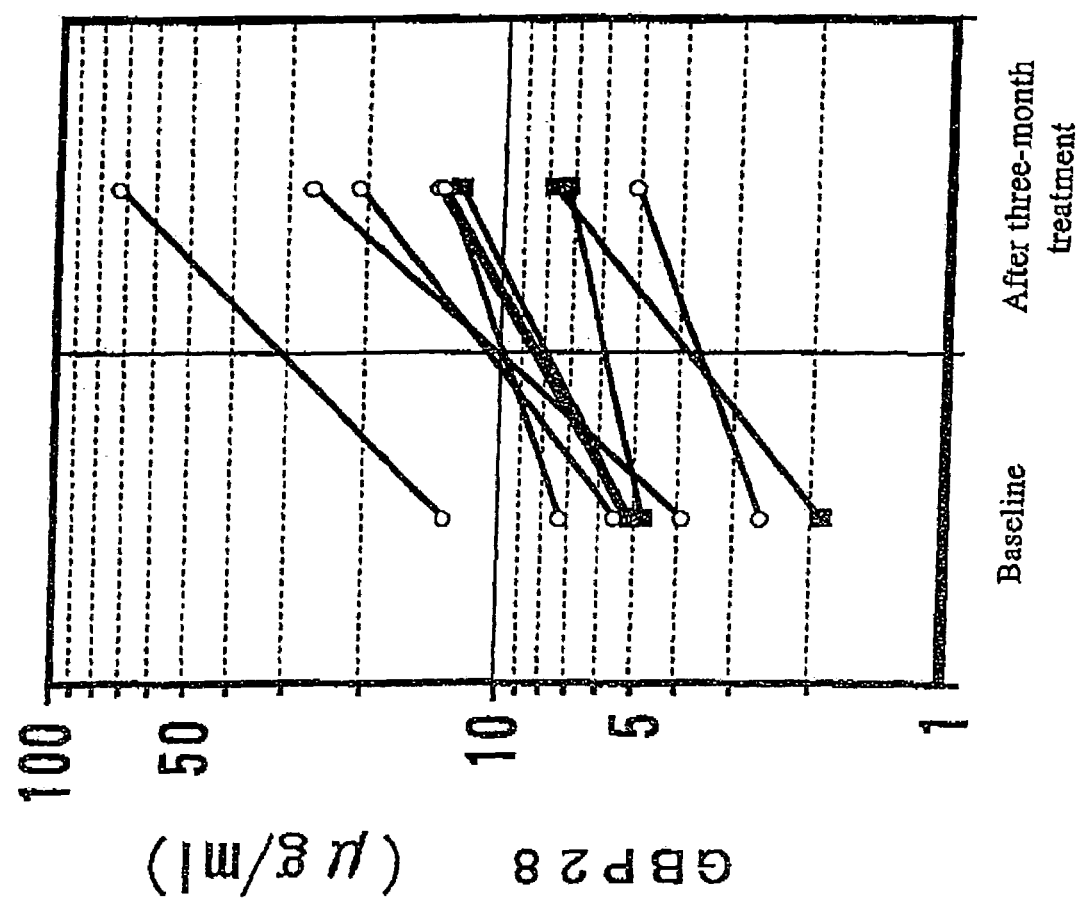
FIG. 2 shows changes in serum adiponectin levels caused by three-month administration of pioglitazone (30 mg/day) to 10 patients afflicted with type II diabetes (Japanese males), wherein "○—○" represents diet therapy and administration of pioglitazone (n=7), and "■—■" represents diet therapy and administration of sulfonylurea and pioglitazone (n=3).

As a result of the three-month administration of pioglitazone, the elevation in the serum adiponectin level was observed in all 10 patients (1.5 to 6.8 times higher than the baselines and 3 times higher on average) (Table 2 and FIG. 2). Further, the rate of changes in GBP28 and in other parameters shown in Tables 2 and 3 generated over the course of three months were examined. The rate of change in the measured value of each parameter (some were logarithmic values) was compared with each other. As a result, it was found that the concentration of GBP28 in the sample exhibited a larger rate of change (80.9%) than levels of blood glucose (18.2%), HbA$_{IC}$ (9.0%), serum insulin (23.7%), HOMA-IR (62.6%), and the like that have been conventionally known as factors associated with type II diabetes.

Example 4

Assay Results of Healthy Subjects

In Example 3, GBP28 was found to be applicable to the monitoring of the therapeutic effects of thiazolidine derivatives. i.e., therapeutic agents for type II diabetes, in patients with type II diabetes. Also, the applicability of the concentration of GBP28 as an indicator of insulin resistance could be predicted. Thus, healthy individuals were subjected to inspection for the association between the blood concentration of GBP28 and parameters that have been reported to be associated with insulin resistance.

980 individuals between the ages of 30 and 65 who annually visit the hospital to get medical checkups were subjected to inspections for the parameters that have been reported to be associated with insulin resistance. Specifically, the subjects were 714 males and 266 females, and patients having endocrine diseases or serious kidney or liver diseases were excluded therefrom. Also, patients who had been on insulin, antidiabetic agents, or antihyperlipidemic agents as medications were excluded.

Parameters, i.e., the systolic blood pressure (SBP) and the diastolic blood pressure (DBP), were measured twice in a sitting position after an at least 5-minute recess. Ages, BMI, cardiac rates, levels of fasting plasma glucose (FPG), serum insulin, adiponectin, total cholesterol (TC), triglyceride (TG), HDL-cholesterol, LDL-cholesterol, and uric acid were measured in the morning after an overnight fast. Levels of plasma glucose and uric acid were measured by a common automated measuring technique. The serum concentration of insulin was measured using a commercially available kit, EIA (Tosoh, Tokyo), as already described. The insulin resistance index was evaluated by the homeostasis model assessment (HOMA-IR).

The results of comparison between each parameter measured in these inspections and GBP28 concerning male subjects are shown in Table 4, and those concerning female subjects are shown in Table 5.

TABLE 4

| vs. log[GBP28] | | A<br>Mean ± SD | B<br>r | P | C<br>Correction depending on age and body mass index<br>r | P | D<br>Correction depending on age and body mass index<br>r | P |
|---|---|---|---|---|---|---|---|---|
| Age | (years) | 46.4 ± 10.1 | 0.044 | NS | — | — | — | — |
| Body Mass Index | (kg/m$^2$) | 23.2 ± 2.7 | −0.354 | <0.0001 | — | — | −0.257 | 0.0069 |
| Body fat | (%) | 21.8 ± 4.8 | −0.369 | <0.0001 | −0.177 | 0.065 | — | — |
| Systolic blood pressure | (mm Hg) | 124 ± 18 | −0.164 | <0.0001 | −0.052 | NS | −0.100 | NS |
| Diastolic blood pressure | (mm Hg) | 77 ± 12 | −0.140 | 0.0002 | −0.047 | NS | −0.064 | NS |
| Cardiac rate | (beats/min) | 75 ± 13 | −0.043 | NS | −0.033 | NS | −0.012 | NS |
| Glucose | (mg/dl) | 95 ± 16 | −0.140 | 0.0002 | −0.067 | 0.068 | −0.057 | NS |
| Insulin (log) | (μU/ml) | 5.58 ± 3.60 | −0.338 | <0.0001 | −0.229 | <0.0001 | −0.362 | <0.0001 |
| HOMA-IR (log) | (—) | 1.33 ± 0.98 | −0.348 | <0.0001 | −0.237 | <0.0001 | −0.362 | <0.0001 |
| Total cholesterol | (mg/dl) | 200 ± 31 | −0.065 | 0.08 | −0.013 | NS | 0.018 | NS |
| Triglyceride (log) | (mg/dl) | 121 ± 84 | −0.344 | <0.0001 | −0.197 | <0.0001 | −0.207 | 0.0005 |
| HDL-cholesterol | (mg/dl) | 54 ± 13 | 0.414 | <0.0001 | −0.330 | <0.0001 | 0.293 | <0.0001 |
| LDL-cholesterol | (mg/dl) | 126 ± 28 | −0.154 | <0.0001 | −0.083 | 0.024 | −0.030 | NS |
| Uric acid | (mg/dl) | 6.2 ± 1.2 | −0.258 | <0.0001 | −0.174 | <0.0001 | −0.214 | 0.0003 |

Data are represented by mean ± S.D..
NS: P > 0.1
n = 330 (relative to body fat)

TABLE 5

| vs. log[GBP28] | | A<br>Mean ± SD | B<br>r | P | C<br>Correction depending on age and body mass index<br>r | P | D<br>Correction depending on age and body mass index<br>r | P |
|---|---|---|---|---|---|---|---|---|
| Age | (years) | 41.7 ± 9.9 | 0.089 | NS | — | — | — | — |
| Body Mass Index | (kg/m$^2$) | 20.7 ± 2.7 | −0.226 | 0.0002 | — | — | 0.214 | NS |
| Body fat | (%) | 21.8 ± 4.8 | −0.360 | <0.0001 | −0.566 | 0.0073 | — | — |
| Systolic blood pressure | (mm Hg) | 112 ± 16 | −0.037 | NS | 0.050 | NS | 0.053 | NS |
| Diastolic blood pressure | (mm Hg) | 68 ± 11 | −0.043 | NS | 0.016 | NS | 0.040 | NS |
| Cardiac rate | (beats/min) | 74 ± 10 | 0.029 | NS | 0.072 | NS | 0.067 | NS |
| Glucose | (mg/dl) | 90 ± 9 | −0.128 | 0.037 | −0.036 | NS | −0.072 | NS |
| Insulin (log) | (μU/ml) | 4.82 ± 2.50 | −0.220 | 0.0003 | −0.137 | 0.040 | −0.127 | NS |
| HOMA-IR (log) | (—) | 1.08 ± 0.61 | −0.225 | 0.0002 | −0.134 | 0.047 | −0.126 | NS |
| Total cholesterol | (mg/dl) | 193 ± 33 | 0.010 | NS | 0.006 | NS | 0.055 | NS |
| Triglyceride (log) | (mg/dl) | 68 ± 37 | −0.306 | <0.0001 | −0.275 | <0.0001 | −0.134 | NS |
| HDL-cholesterol | (mg/dl) | 69 ± 15 | 0.393 | <0.0001 | 0.345 | <0.0001 | 0.280 | 0.0007 |
| LDL-cholesterol | (mg/dl) | 112 ± 28 | −0.175 | 0.0042 | −0.199 | 0.0041 | −0.131 | NS |
| Uric acid | (mg/dl) | 4.3 ± 0.94 | −0.018 | NS | −0.025 | NS | 0.014 | NS |

Data are represented by mean ± S.D..
NS: P > 0.1
n = 330 (relative to body fat)

In these tables, data are represented by "mean±S.D.," correlation coefficients, and p values. The blood GBP28 exhibited a wide range of concentration distributions from 0.4 μg/ml to 61.2 μg/ml. The blood concentrations of GBP28 of male subjects were 7.2±4.6 μg/ml, and those of female subjects were 13.3±7.3 μg/ml. That is, female subjects exhibited higher concentration of GBP28 than male subjects.

As shown in Tables 4 and 5, the blood concentration of GBP28 exhibited negative correlations with BMI, the systolic blood pressure, the diastolic blood pressure, fasting plasma glucose, insulin, HOMA-IR, triglyceride, LDL-cholesterol, and uric acid. The blood concentration of GBP28 exhibited positive correlations with HDL-cholesterol. When corrections were made depending on age and BMI and comparisons between GBP28 and each parameter were conducted, statistically significant correlations were attained with a reliability of p<0.05, i.e., regarding insulin (male: r=−0.229, female: r=−0.137), HOMA-IR (male: r=−0.237, female: r=−0.134), triglyceride (male: r=−0.197, female: r=−0.275), HDL-cholesterol (male: r=−0.330, female: r=0.345), and LDL-cholesterol (male: r=−0.083, female: r=−0.199). Therefore, the blood concentration of GBP28 exhibited correlations with HOMA-IR, insulin, triglyceride, HDL-cholesterol, and LDL-cholesterol.

As a result, it was found that the concentration of GBP could also serve as an indicator of insulin resistance for healthy individuals.

Example 5

Production of a Kit for Assaying Naturally Occurring GBP28 in a Sample

A. Materials for the Kit According to the Present Invention (1) A Plate Coated with an Anti-Human GBP28 Monoclonal Antibody A Solution of Anti-Human GBP28 Monoclonal Antibody The anti-human GBP28 monoclonal antibody obtained by processing mouse ascites with FEAE-Sepharose Fast Flow was adjusted to 10 μg/ml with the aid of 0.1M phosphate buffer (pH 7.0).

Composition of Washing Liquid for Preparation of a Plate

TABLE 6

| Reagent | Concentration |
| --- | --- |
| $NaH_2PO_4 \cdot 2H_2O$ | 40 mM |
| $Na_2HPO_4 \cdot 12H_2O$ | 60 mM |
| Tween 20 | 0.05% |
| pH 7.0 | — |

Composition of Block Solution

TABLE 7

| Reagent | Concentration |
| --- | --- |
| $NaH_2PO_4 \cdot 2H_2O$ | 40 mM |
| $Na_2HPO_4 \cdot 12H_2O$ | 60 mM |
| BSA | 1.0% |
| pH 7.0 | — |

1. Fractionate an antibody solution at 120 μl/well on the MaxiSorp F8 plate (Nunc) and then allow the plate to stand at 4° C overnight.
2. Remove the antibody solution and then wash the plate twice with a washing liquid.
3. Fractionate a block solution at 200 μl/well and then allow the plate to stand at 37° C. overnight.
4. Remove the block solution.
5. Allow the plate to stand under reduced pressure overnight, dry it thoroughly, seal it hermetically, and then store it at 4° C.

(2) Standard Solution

Solution of GBP28 Antigen

GBP28 was purified from the serum pooled from healthy individuals using an affinity column to which the anti-human GBP28 monoclonal antibody had been bound. Thereafter, gel filtration was further carried out. The concentration of GBP28 was determined based on the absorbance at 280 nm (the concentration at Abs. 280 nm=1,000 was determined to be 1.0 mg/ml).

Dilution buffer

TABLE 8

| Reagent | Concentration |
| --- | --- |
| $NaH_2PO_4 \cdot 2H_2O$ | 4 mM |
| $Na_2HPO_4 \cdot 12H_2O$ | 16 mM |
| BSA | 1.0% |
| pH 7.4 | — |

The solution of GBP28 antigen was diluted with the aid of the dilution buffer having the above composition. Thus, the concentration of GBP28 was set at 0, 2, 5, 10, 25, and 50 ng/ml.

(3) Solution of Peroxidase-Labeled Anti-Human GBP28 Monoclonal Antibody

Stock Solution of Peroxidase-Labeled Anti-Human GBP28 Monoclonal Antibody

The anti-human GBP28 monoclonal antibody was subjected to pepsin digestion and reduction treatment to prepare the Fab' fragment, and maleimide-activated peroxidase was allowed to bind thereto. The concentration was calculated by determining each concentration of the anti-human GBP28 monoclonal antibody at the Fab' site and at the peroxidase site based on absorbance at 280 nm and 403 nm and adding them up.

Solution for Diluting a Labeled Antibody

TABLE 9

| Reagent | Concentration |
| --- | --- |
| $NaH_2PO_4 \cdot 2H_2O$ | 4 mM |
| $Na_2HPO_4 \cdot 12H_2O$ | 16 mM |
| BSA | 1.0% |
| pH 6.5 | — |

The solution of peroxidase-labeled anti-human GBP28 monoclonal antibody was diluted with the aid of a solution for diluting a labeled antibody having the above composition, and the concentration of the labeled antibody was set at 350 ng/ml. Thus, a solution of peroxidase-labeled anti-human GBP28 monoclonal antibody was prepared.

(4) Concentrated Washing Liquid (Diluted 20-Fold with Purified Water at the Time of Use)

TABLE 10

| Reagent | Concentration |
| --- | --- |
| $NaH_2PO_4 \cdot 2H_2O$ | 40 mM |
| $Na_2HPO_4 \cdot 12H_2O$ | 60 mM |
| Tween 20 | 1.0% |
| pH 6.5 | — |

(5) Substrate Solution

A commercially available tetramethylbenzidine (TMB) solution for ELISA was used.

(6) Reaction Terminator 0.36N $H_2SO_4$ was used.

B. Assay Protocol

Specimens to be tested are diluted to suitable concentrations (up to 50 ng/ml) with the aid of the dilution buffer which was used for preparation of the standard solution. The dilution ratio of general specimens may be suitably about 400- to fold (e.g., 21-fold dilution is repeated twice to attain 441-fold dilution).

1. Place a standard solution and a specimen to be tested in the wells of a plate (100 μl/well).
2. Stir for about 5 to 10 seconds via a plate stirrer and then allow the plate to stand at room temperature under light-shielded conditions for 60 minutes.
3. Remove the standard solution and the specimen and wash the plate four times with a washing liquid.
4. Place a solution of peroxidase-labeled antibody in the wells of a plate (100 μl/well).

5. Stir for about 5 to 10 seconds via a plate stirrer and then allow the plate to stand at room temperature under light-shielded conditions for 30 minutes.

6. Remove the solution of peroxidase-labeled antibody and wash the plate four times with a washing liquid.

7. Place a substrate solution in the wells of a plate (100 μl/well).

8. Stir for about 5 to 10 seconds via a plate stirrer and then allow the plate to stand at room temperature under light-shielded conditions for 30 minutes.

9. Place a reaction terminator in the wells of a plate (100 μl/well).

10. Stir for about 5 to 10 seconds via a plate stirrer and assay the absorbance of each well (assay wavelength: 450/650 nm (primary/secondary), approximate expression for calibration curve: quadratic).

Example 6

Preparation of Calibration Curve

Figure 3:
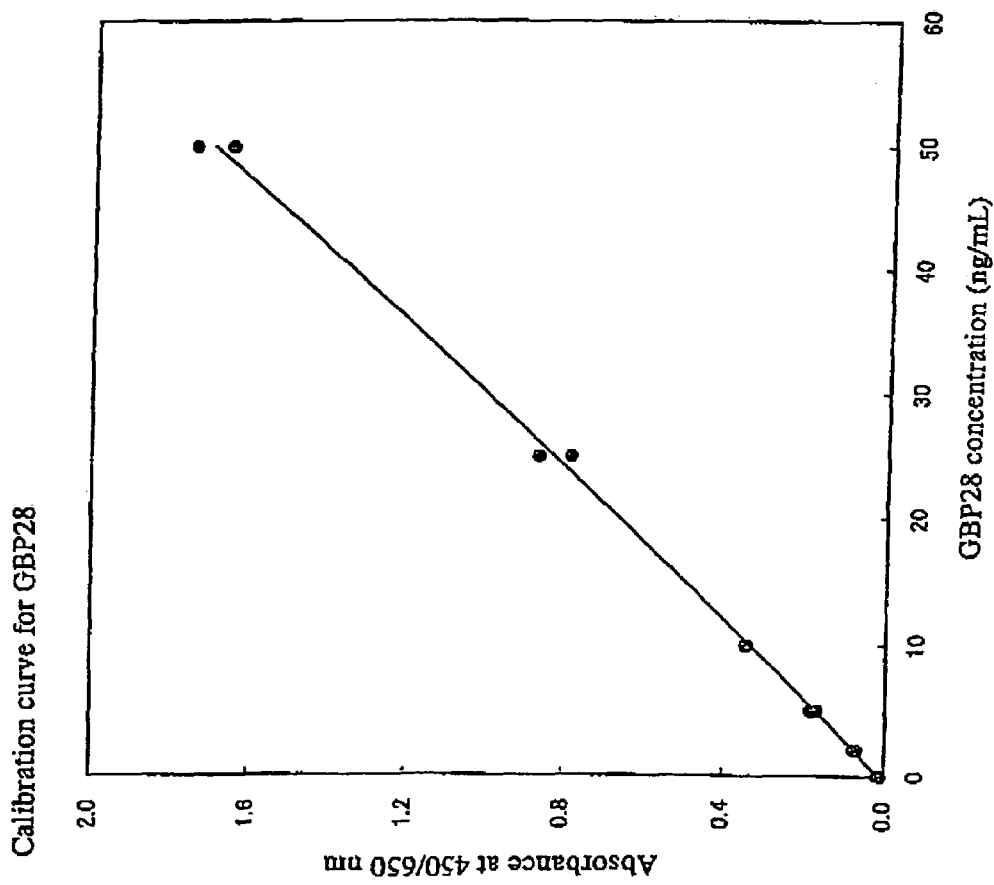
FIG. 3 shows the calibration curve for GBP28.

Prepared standard solutions of 0, 2, 5, 10, 25, and 50 ng/ml of GBP28 were assayed as samples, and the calibration curve was inspected. As shown in FIG. 3, the obtained calibration curve was substantially linear. Since the average concentration of GBP28 in the blood was 10 μg/ml, the specimen was subjected to 21-fold dilution twice to attain 441-fold dilution. Assay was conducted at this concentration (assay range: 0 to 22 μg/ml).

Example 7

Test for Repeatability

In order to evaluate changes in the assay values obtained by the kit, 3 types of serum samples were used, and each thereof was subjected to assay 24 times. As a result, the CV values were satisfactorily 5% or lower as shown in Table 11. Thus, the assay values obtained by the kit of the present invention could be determined to be reliable.

TABLE 11

Repeatability of GBP28 assay

GBP28 (μg/ml)

|  | A | B | C |
|---|---|---|---|
| 1 | 4.95 | 8.25 | 15.26 |
| 2 | 5.93 | 8.59 | 13.61 |
| 3 | 5.82 | 6.64 | 14.82 |
| 4 | 5.63 | 8.11 | 12.99 |
| 5 | 5.86 | 7.93 | 14.59 |
| 6 | 5.96 | 7.67 | 13.34 |
| 7 | 5.55 | 7.50 | 14.56 |
| 8 | 5.46 | 7.78 | 13.53 |
| 9 | 5.55 | 7.47 | 14.70 |
| 10 | 5.62 | 7.92 | 13.48 |
| 11 | 5.17 | 7.97 | 13.59 |
| 12 | 5.80 | 7.48 | 15.00 |
| 13 | 5.94 | 8.15 | 14.29 |
| 14 | 5.39 | 7.99 | 15.04 |
| 15 | 5.84 | 7.78 | 14.22 |
| 16 | 5.46 | 7.82 | 14.22 |
| 17 | 5.53 | 8.09 | 14.59 |
| 18 | 5.85 | 7.68 | 14.01 |
| 19 | 6.01 | 7.75 | 14.32 |
| 20 | 5.88 | 8.18 | 14.88 |
| 21 | 5.63 | 7.83 | 13.13 |
| 22 | 5.80 | 8.28 | 15.15 |
| 23 | 6.21 | 8.41 | 15.33 |

TABLE 11-continued

Repeatability of GBP28 assay

GBP28 (μg/ml)

|  | A | B | C |
|---|---|---|---|
| 24 | 5.82 | 8.08 | 14.80 |
| N | 24 | 24 | 24 |
| MAX. | 6.21 | 8.59 | 15.33 |
| MIN. | 4.95 | 6.64 | 12.99 |
| MEAN | 5.694 | 7.889 | 14.309 |
| S.D. | 0.2762 | 0.3834 | 0.6883 |
| C.V. | 4.8% | 4.9% | 4.8% |

Example 8

Test for Day-to-Day Repeatability

In order to evaluate day-to-day variations generated in the assay values obtained by the kit, 5 types of serum samples were used, and each thereof was subjected to the assay five times on five separate days. As a result, variations in the assay values for 5 days were satisfactorily of a c.v. of 3.3% to 6.8% as shown in Table 12. Thus, the assay values obtained by the kit of the present invention could be determined to be reliable.

TABLE 12

Day-to-day repeatability of GBP28 assay

GBP28 (μg/ml)

|  | A | B | C | D | E |
|---|---|---|---|---|---|
| 1 | 7.67 | 5.88 | 5.38 | 15.98 | 11.91 |
| 2 | 8.24 | 5.61 | 5.37 | 16.19 | 12.12 |
| 3 | 8.08 | 5.85 | 6.00 | 14.58 | 11.49 |
| 4 | 8.44 | 6.00 | 5.72 | 15.88 | 11.86 |
| 5 | 7.26 | 5.32 | 4.89 | 14.93 | 11.04 |
| N | 5 | 5 | 5 | 5 | 5 |
| MAX. | 8.44 | 6.00 | 6.00 | 16.19 | 12.12 |
| MIN. | 7.26 | 5.32 | 4.89 | 14.58 | 11.04 |
| MEAN | 7.937 | 5.730 | 5.471 | 15.514 | 11.684 |
| S.D. | 0.4220 | 0.2432 | 0.3736 | 0.6366 | 0.3835 |
| C.V. | 5.3% | 4.2% | 6.8% | 4.1% | 3.3% |

Example 9

Dilution Test

In order to avoid the influence of the serum component on the reaction system, the serum sample is usually diluted and then used for an assay when the diagnostic agent kit is used. In order to confirm that the dilution ratio is optimal, a sample at a given concentration is suitably diluted and then assayed, and whether or not the obtained values result in a straight line on the graph is determined. A straight line indicates that the properties of the sample are equivalent to those of the standard solution. The assay values are determined not to be affected by the serum component.

Figure 4:
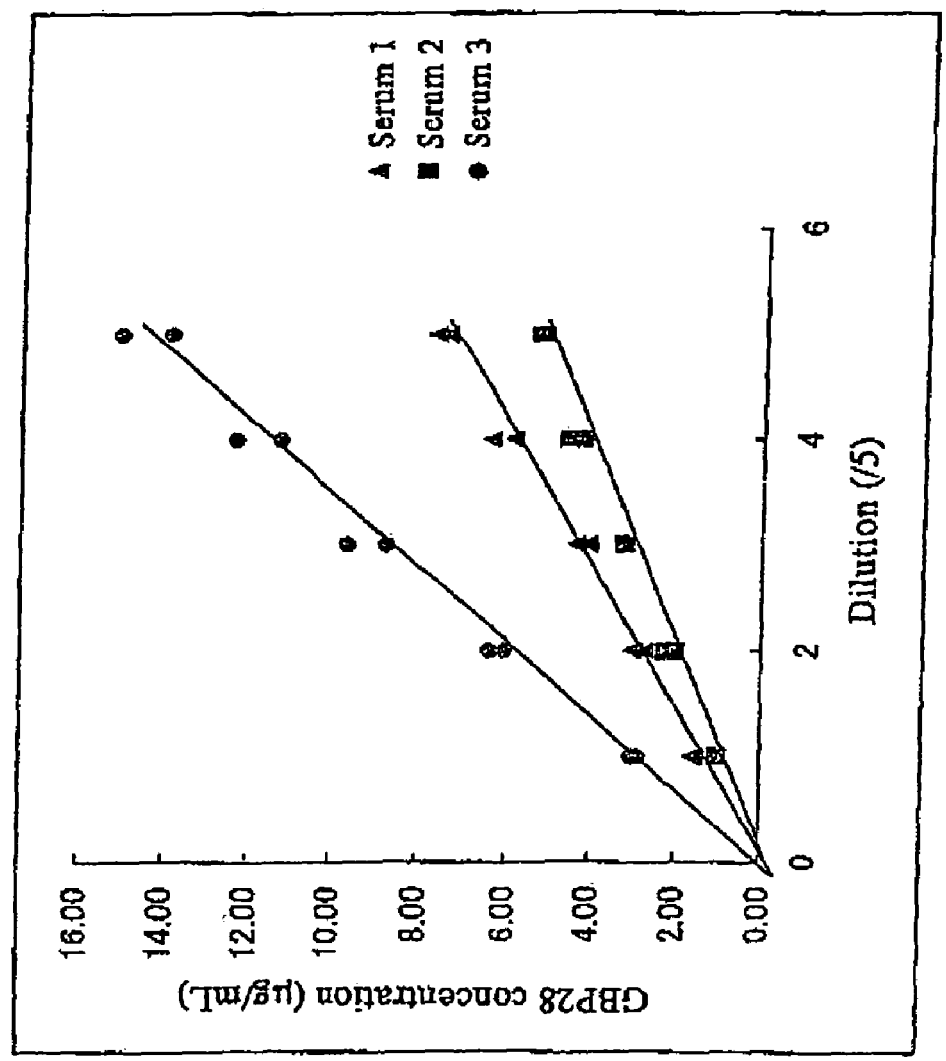
FIG. 4 shows the dilution linearity for GBP assay.

Three types of serum samples were diluted 441-fold in accordance with the assay protocol, these samples were further diluted to 1/5 to 5/5, and each thereof was subjected to the assay twice. As a result, all the specimens exhibited good linearity as shown in Table 13 and FIG. 4. This indicated that the dilution ratio of the kit was appropriate.

TABLE 13

Dilution linearity of GBP28 assay Serum 1

| Dilution (/5) | GBP28 concentration (μg/ml) Serum 1 | GBP28 concentration (μg/ml) Serum 2 | GBP28 concentration (μg/ml) Serum 3 |
|---|---|---|---|
| 1 | 1.54 | 1.00 | 2.88 |
| 1 | 1.59 | 1.05 | 3.00 |
| 2 | 2.73 | 2.28 | 6.41 |
| 2 | 2.99 | 2.03 | 6.05 |
| 3 | 4.36 | 3.24 | 9.63 |
| 3 | 4.08 | 3.21 | 8.75 |
| 4 | 6.43 | 4.60 | 12.34 |
| 4 | 5.88 | 4.25 | 11.28 |
| 5 | 7.45 | 5.20 | 15.04 |
| 5 | 7.68 | 5.32 | 13.88 |

Example 10

Addition-Recovery Test

Unlike isolated proteins, proteins that are present in blood may form a complex with various other proteins or substances existing in blood, or undergo changes in their confirmations. Even though good evaluation results were obtained from a standard sample prepared from a isolated protein at a suitable concentrations, therefore, an accurate concentration could not always be obtained when serum or the like was employed as a sample (for example, the formation of a complex results in the loss of an epitope to the antibody).

Thus, samples were prepared by adding a GBP28 standard solution adjusted to a suitable concentration to sample serum, and the resulting samples were subjected to the assay. Subsequently, the concentration level of the sample before the addition of the standard sample was subtracted from the obtained value, the resultant was divided by the amount added, and the recovery rate was thus determined. As a result, a good recovery rate of approximately 95% on average was obtained as shown in Table 14. Thus, it was demonstrated that this kit was able to be used for conducting the assay without the influence of the blood component on the added standard sample. This also verified that the blood concentration of GBP28 could be accurately assayed.

TABLE 14

Results of addition-recovery test

|  | None | A | B | C |
|---|---|---|---|---|
| Serum 1 | | | | |
| Mean (μg/ml) | 10.34 | 11.85 | 13.98 | 19.90 |
| Amount added (μg/ml) | — | 1.52 | 3.65 | 9.57 |
| Recovery rate (%) | — | 93.4 | 95.6 | 91.9 |
| Serum 2 | | | | |
| Mean (μg/ml) | 13.73 | 15.25 | 17.75 | 23.16 |
| Amount added (μg/ml) | — | 1.52 | 4.02 | 9.43 |
| Recovery rate (%) | — | 93.8 | 105.3 | 90.6 |
| Serum 3 | | | | |
| Mean (μg/ml) | 26.36 | 28.13 | 30.56 | 36.88 |
| Amount added (μg/ml) | — | 1.77 | 4.20 | 10.52 |
| Recovery rate (%) | — | 109.1 | 110.1 | 101.1 |

INDUSTRIAL APPLICABILITY

The present invention enables the simple diagnosis of carbohydrate metabolism disorders, such as type II diabetes, in the clinical field by assaying the concentration of GBP28 in a sample. Also, the present invention enables the monitoring of the therapeutic effects of an agent for type II diabetes, particularly, a thiazolidine derivative. Furthermore, the use of the antibody according to the present invention enables the assay of the blood concentration of GBP28, preferably naturally-occurring GBP28, and GBP28 can be quantitatively assayed without pretreatment, such as thermal treatment, of the GBP28 in the sample. This can lead to simplified assay processes and improved abilities to process specimens.

Further, the method according to the present invention can easily process a large amount of specimens. Thus, a very effective assay system is provided, which can be employed in clinical examinations for geriatric diseases associated with insulin resistance, such as diabetes, elevated blood pressure, hyperlipidemia, or arteriosclerosis.

All publications, patents, and patent applications cited herein are incorporated herein by reference in their entirety.

The invention claimed is:

1. A monoclonal antibody or fragment thereof, which does not bind with a monomeric structure of adiponectin (GBP28) but specifically binds with GBP28 having a trimer structure of GBP28 and/or a structure of aggregated GBP28 trimers.

2. The monoclonal antibody or fragment thereof according to claim 1, wherein the structure of aggregated GBP28 trimers consists of from 4 to 6 GBP28 trimers.

3. A kit or reagent for measuring a level of GBP28, which comprises the monoclonal antibody or fragment thereof according to claim 1.

4. A monoclonal antibody or fragment thereof, which does not bind with a monomeric structure of GBP28 but specifically binds with GBP28 having a trimer structure of GBP28 and/or a structure of aggregated GBP28 trimers, wherein said monoclonal antibody recognizes an epitope which appears when the trimer structure of GBP28 is formed.

5. The monoclonal antibody or fragment thereof according to claim 4, wherein the structure of aggregated GBP28 trimers consists of from 4 to 6 GBP28 trimers.

6. A kit or reagent for measuring a level of GBP28, which comprises the monoclonal antibody or fragment thereof according to claim 4.

* * * * *